US006918695B2

(12) United States Patent
Polegato Moretti et al.

(10) Patent No.: US 6,918,695 B2
(45) Date of Patent: Jul. 19, 2005

(54) APPARATUS FOR MEASURING THE BREATHABILITY AND COMFORT OF A SHOE

(75) Inventors: Mario Polegato Moretti, Crocetta del Montello (IT); Bruno Mattioni, Udine (IT); Antonio Ferrarese, Isola Della Scala (IT)

(73) Assignee: GEOX S.p.A., Montebelluna (IT)

( * ) Notice: Subject to any disclaimer, the term of this patent is extended or adjusted under 35 U.S.C. 154(b) by 0 days.

(21) Appl. No.: 10/614,041

(22) Filed: Jul. 8, 2003

(65) Prior Publication Data

US 2004/0008751 A1 Jan. 15, 2004

(30) Foreign Application Priority Data

Jul. 9, 2002 (IT) ........................... PD2002A0186

(51) Int. Cl.⁷ .................... G01N 3/00; G01K 13/00; G01K 7/00
(52) U.S. Cl. .................. 374/47; 374/51; 374/45; 374/142
(58) Field of Search .................. 374/45, 46, 47, 374/51, 141, 142, 179, 52

(56) References Cited

U.S. PATENT DOCUMENTS 1,015,291 A * 1/1912 Byrnes ........................... 12/4.1
4,130,007 A * 12/1978 Hayashi ........................... 73/7
4,327,572 A * 5/1982 Pitman et al. .................... 73/7
4,432,223 A * 2/1984 Paquette et al. .................. 73/7
4,961,339 A * 10/1990 Kleis et al. ....................... 73/73
5,749,259 A * 5/1998 Hamouda et al. ............. 73/159
5,979,235 A * 11/1999 Kurz et al. ................. 73/432.1
6,487,891 B2 * 12/2002 Moretti .......................... 73/38
2003/0156619 A1 * 8/2003 De Monte et al. ............ 374/44

FOREIGN PATENT DOCUMENTS

| EP | 264526 A2 * | 4/1988 | .......... G01N/19/02 |
| GB | 2 272 511 A | 5/1994 | |
| GB | 2 272 528 A | 5/1994 | |
| JP | 06323963 A * | 11/1994 | .......... G01M/19/00 |

* cited by examiner

Primary Examiner—Gail Verbitsky
Assistant Examiner—Mirellys Jagan
(74) Attorney, Agent, or Firm—Oblon, Spivak, McClelland, Maier & Neustadt, P.C.

(57) ABSTRACT

An apparatus for measuring the breathability and comfort level of a shoe, comprising a rigid structure that duplicates the contour of a foot, divided into at least three thermally insulated regions from each other, for the shoe to be tested, resistors heating the regions of the rigid structure to a presettable temperature, at least one cladding of a soft material permeable to liquids, that absorb water and distributing it over the entire surface of the structure, sensors for sensing the temperature of cladding regions corresponding to the contour regions, a metering pump to supply water to the structure, and a power measuring device.

83 Claims, 7 Drawing Sheets

APPARATUS FOR MEASURING THE BREATHABILITY AND COMFORT OF A SHOE

BACKGROUND OF THE INVENTION

The present invention relates to an improved apparatus for measuring the breathability of a shoe and its level of comfort.

It is known that human perspiration occurs by expelling sweat through the pores of the skin, which are each connected to sweat glands.

The generated sweat is liquid, and once it has made contact with the warm skin it evaporates, removing its own latent heat of evaporation (approximately 580 calories/g at 30° C.).

This fact cools the skin and activates body thermoregulation.

Some systems commonly used to measure the breathability of items of clothing or shoes relate only to the materials that compose them.

These systems allow to obtain data related to breathability defined in milligrams per square centimeter per hour, or in grams per square meter per day.

The basic conditions of the tests are defined for example in the UNI 8429 standard, but they cannot be applied for example to an entire shoe, since they do not provide the necessary conditions such as the presence of multiple layers, the movement of the foot and the different sweat production conditions.

A complex simulation system has also been devised which is based on the measurement of the difference in breathability between a water-resistant but non-breathable article and an article provided with a waterproof and breathable membrane, a system which is therefore partly capable of simulating the generation of vapor by the human foot and therefore of measuring the vapor permeability of a shoe.

This system is disclosed in U.S. Pat. No. 4,918,981, which relates indeed to a method and an apparatus for testing items to be worn, such as for example shoes, gloves, et cetera, that form closed elements for transmitting the vapor generated by perspiration.

The apparatus comprises a thin, flexible and waterproof closed jacket, which is highly vapor-permeable, is inserted in the item to be tested and is filled with water.

The water can be heated in order to simulate the temperature of the body and produce a high concentration of moist vapor inside the item.

The amount of humidity transferred to the environment outside the item being tested and the amount of humidity absorbed and condensed in the item can be measured by means of weight differences on measurements made before, during and after the test period.

Still, the application of this system to shoes does not yield uniform and reliable results, since the actual operating conditions to which the foot is subjected, particularly during walking and/or running, are not simulated, and because the microclimate that occurs inside a shoe during use is not replicated.

Other devices are also known which are capable of producing sweat (vapor) in a known quantity, but their adjustment systems are not precise enough to be self-adjusting and in any case do not replicate the actual heat exchange and vapor exchange phenomena that occur in a foot-shoe system.

An apparatus for measuring the breathability of a shoe has also been devised recently and is disclosed in U.S. Pat. No. 6,487,891; such apparatus comprises, on a supporting footing, a hollow body made of self-supporting material, that reproduces the contour of a foot adapted to support the shoe to be tested.

The body has through holes that are distributed thereon and contains water.

A sock made of waterproof and breathable material (membrane) is arranged so as to enclose the hollow body.

A presser element is provided in order to perform relative movements with the hollow body between a spaced configuration and a configuration in which it is compressed against the sole of the shoe.

The apparatus further comprises means for heating the water in the hollow body to a preset and constant temperature and means for measuring the weight of such hollow body together with everything that is associated therewith and the shoe to be tested.

Such apparatuses, and in particular the last one, which in practice has proved to be qualitatively the best, despite constituting technological steps forward, have been found to suffer drawbacks, including:

difficulty in inserting the shoe easy rupture of the sock during the test, accordingly causing losses of liquid that alter the results poor accuracy of the adjustment of the internal temperature, which in any case cannot be diversified according to the various regions of the foot impossibility to adjust the amount of vapor generated independently of the temperature values impossibility to determine the corresponding values of internal relative humidity between the shoe and the artificial foot generated after supplying a known amount of water poor reproducibility of the data (VC<20%), which makes the data scarcely significant and usable non-reproducibility of the actual physiological phenomenon of perspiration.

It should also be noted that in any case it is not possible to determine the amount of heat, or more generally the energy dissipated by a shoe-foot system.

SUMMARY OF THE INVENTION

The aim of the present invention is to provide an apparatus that is capable of simulating the mass and energy exchanges that occur in the human foot and can therefore measure the breathability performance of shoes.

Within this aim, an object of the invention is to provide an apparatus that is capable of predicting the value of vapor permeability, water absorption, heat dissipation of a shoe, avoiding subjective thermophysiological tests.

Another object of the invention is to provide an apparatus that is capable of reproducing exactly the microclimate generated inside a shoe.

Still another object is to provide an apparatus that is structurally simple and easy to use.

This aim and these and other objects that will become better apparent hereinafter are achieved by an improved apparatus for measuring the breathability and the level of comfort of a shoe, characterized in that it comprises:

a rigid structure made of self-supporting heat-conducting material that duplicates the contour of a foot, is divided into at least three regions that are thermally insulated from each other, and supports the shoe to be tested;

means for heating autonomously each one of said regions of said rigid structure to a presettable temperature;

at least one cladding made of a soft material whose structure is permeable to liquids and is capable of absorbing water and distributing it over the entire surface of the rigid structure that it surrounds;

means for sensing the external temperature of each one of the regions of said at least one cladding that correspond to the regions of said contour;

means for the metered supply of water to said structure with its claddings;

means for determining the power dissipated in order to keep constant the temperature of said regions.

BRIEF DESCRIPTION OF THE DRAWINGS

Further characteristics and advantages of the apparatus according to the present invention will become better apparent from the detailed description of an embodiment thereof, illustrated by way of non-limitative example in the accompanying drawings, wherein.

DESCRIPTION OF THE PREFERRED EMBODIMENTS

Figure 1:
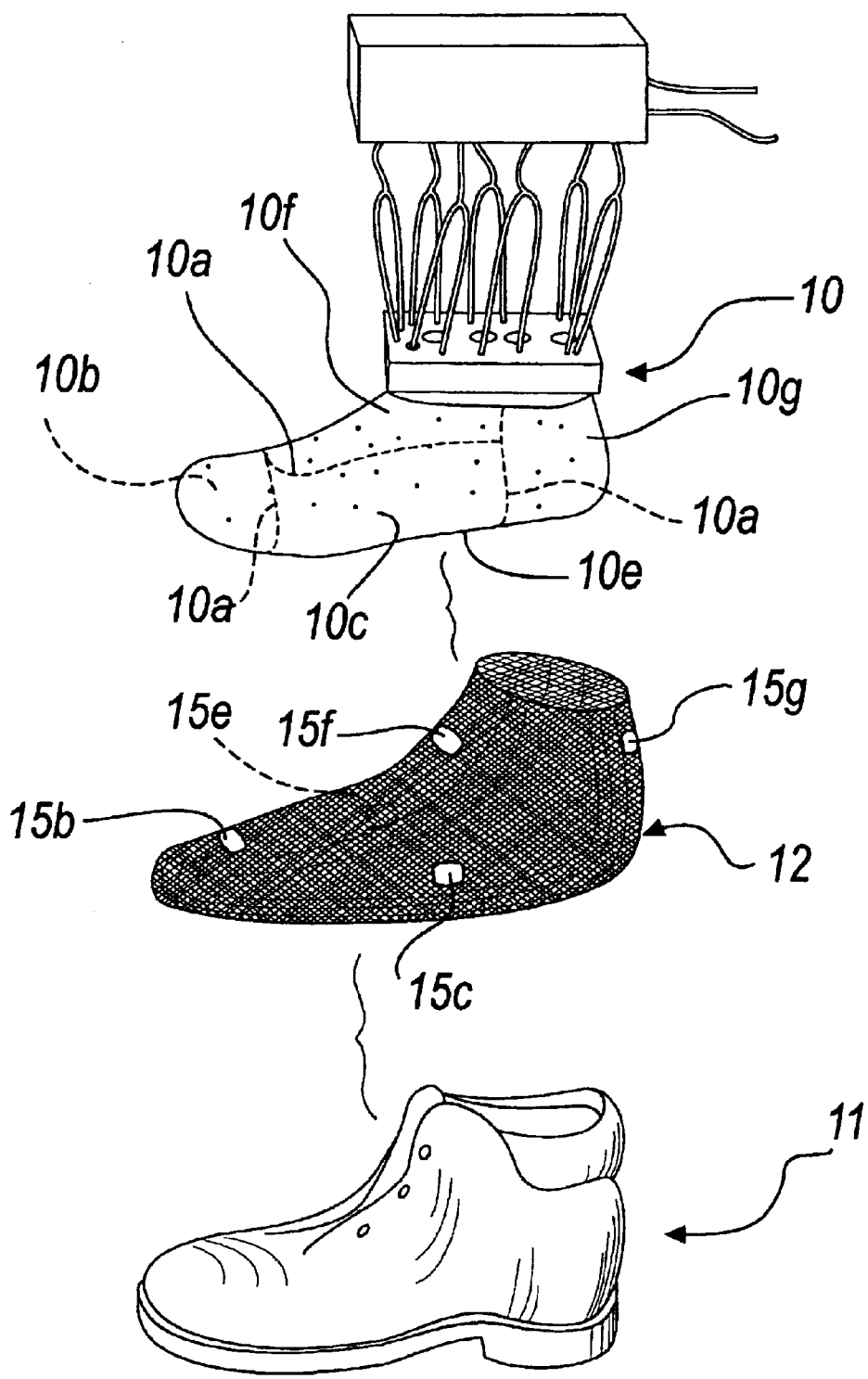
FIG. 1 is an exploded view of a part of the apparatus according to the invention.
Figure 2:
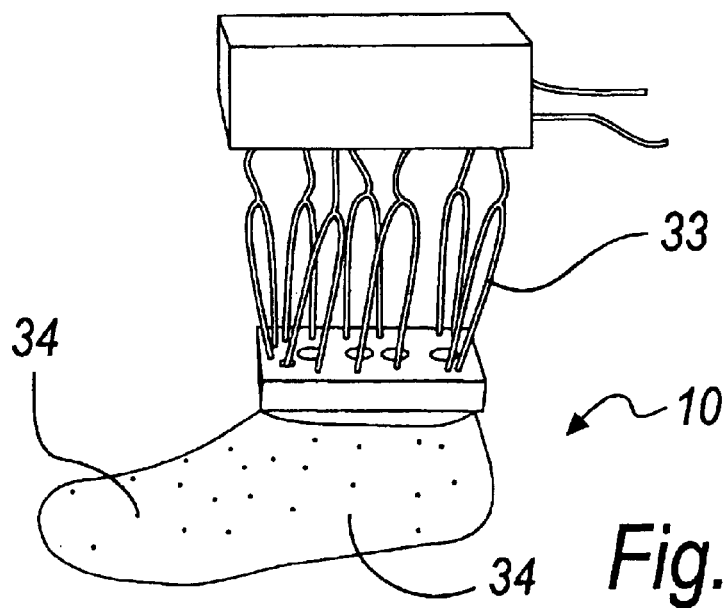
FIG. 2 is a perspective view of a supporting structure that duplicates the contour of a foot, comprised within the apparatus according to the invention.
Figure 3:
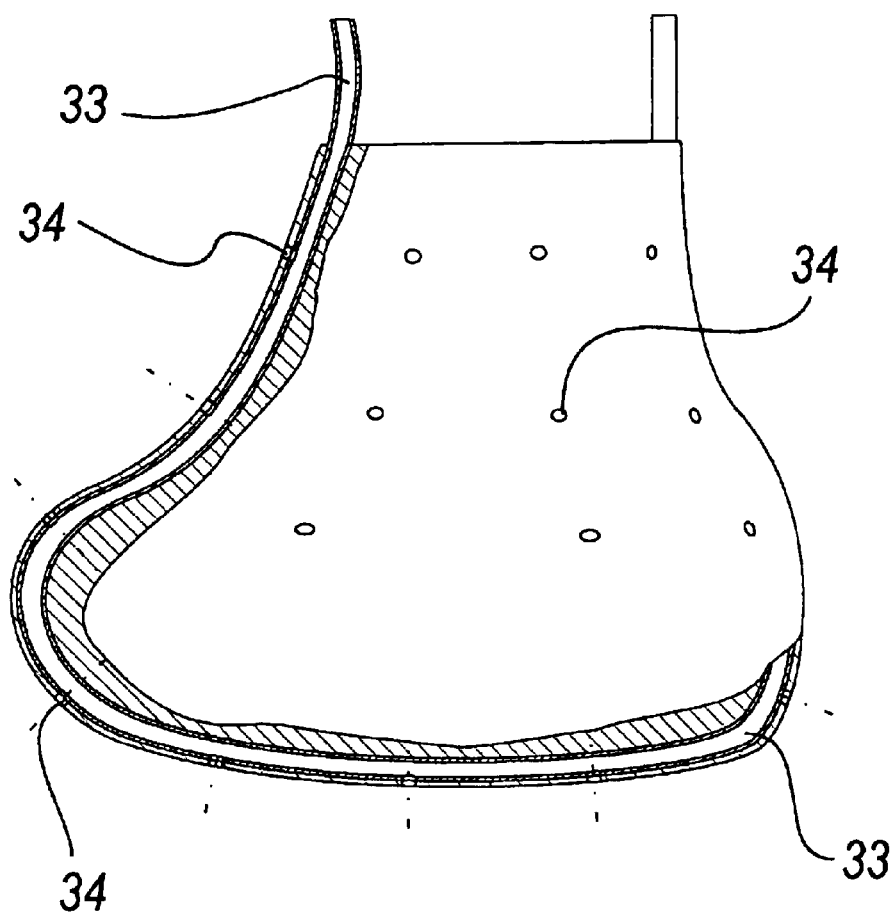
FIG. 3 is a transverse sectional view of the structure of FIG. 2.
Figure 4:
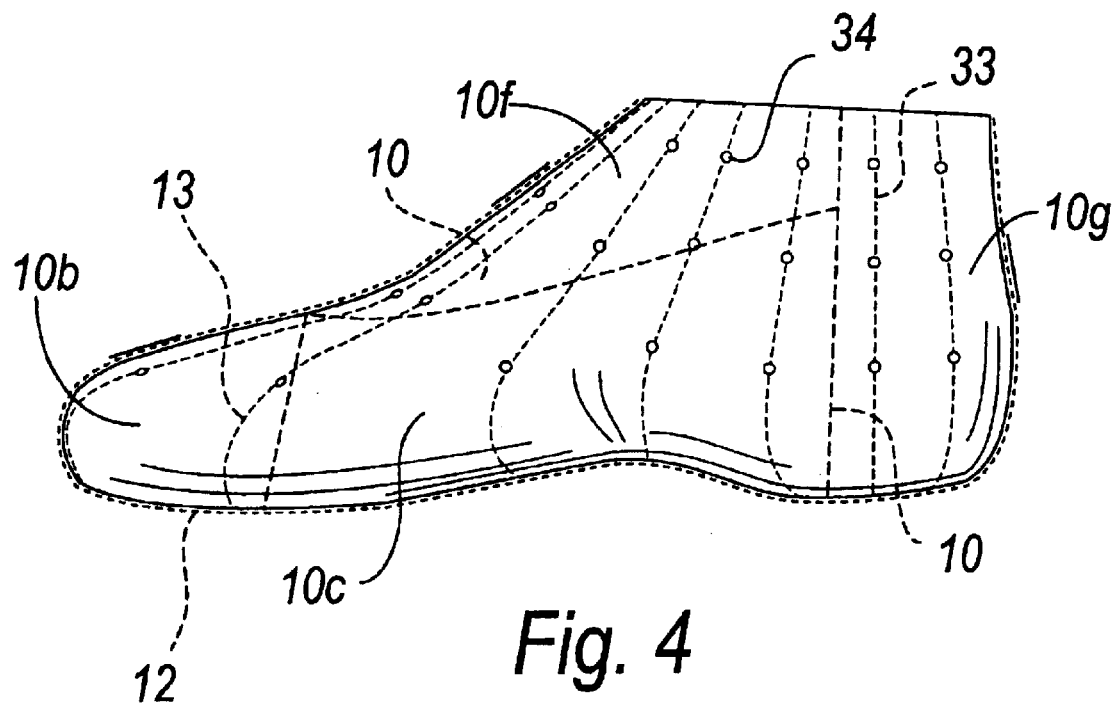
FIG. 4 is a side view of part of the structure of FIG. 2.
Figure 5:
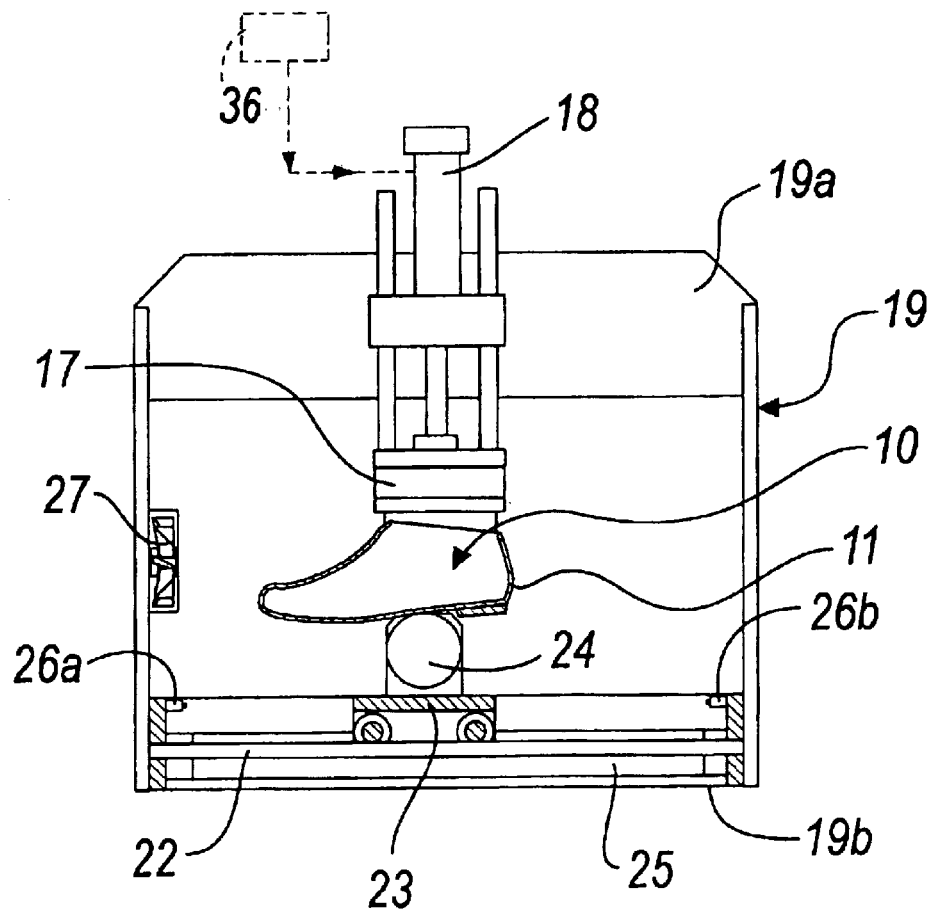
FIG. 5 is a schematic side view of the apparatus according to the invention.
Figure 6:
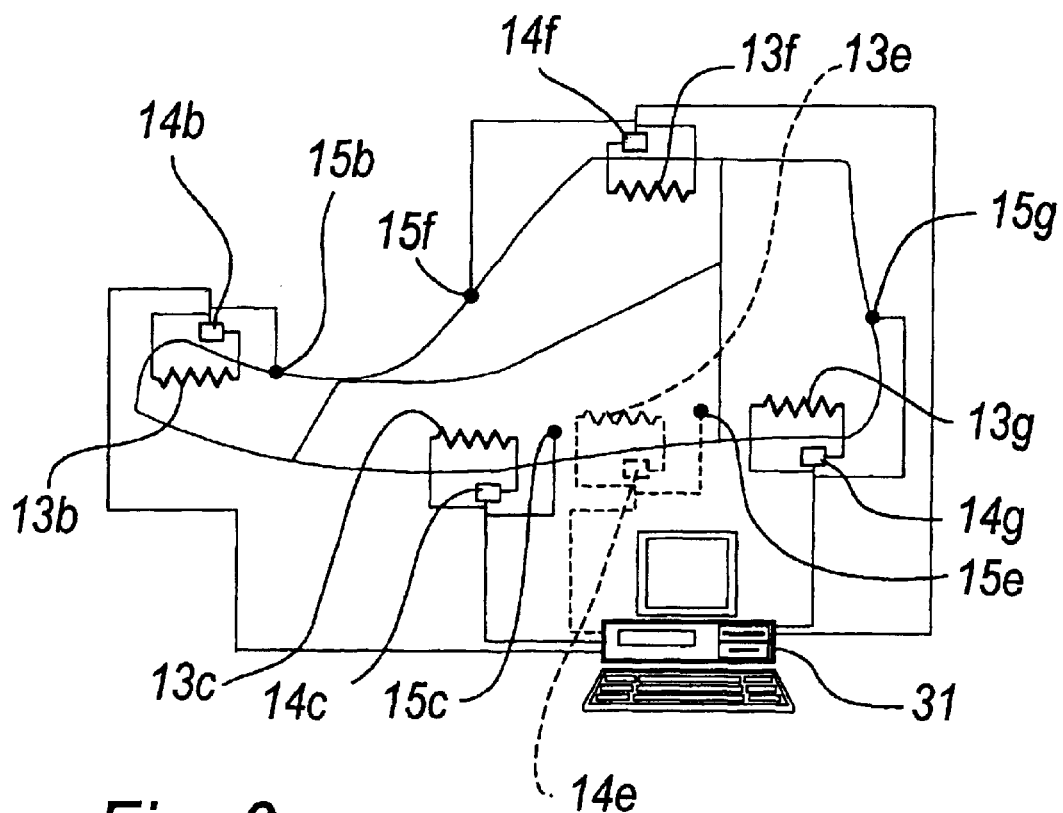
FIG. 6 is a functional diagram of part of the apparatus according to the invention.
Figure 7:
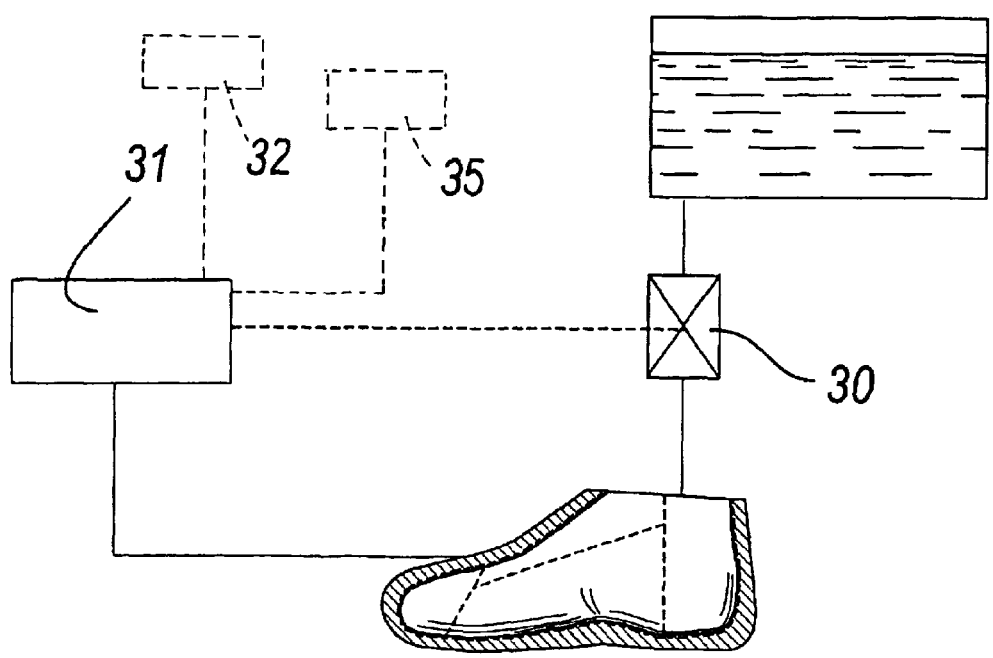
FIG. 7 is a schematic block diagram of the apparatus.

With reference to the figures, an improved apparatus for measuring the breathability of a shoe comprises a central rigid structure 10 made of heat-conducting self-supporting material, such as aluminum or the like, which reproduces the contour of a foot and is designed to support the shoe to be tested, which is designated by the reference numeral 11.

The structure 10 is divided into at least three regions that are thermally insulated from each other and correspond to regions of the foot where differences in thermal conditions have been observed experimentally.

As mentioned in the case being considered, it is preferable to divide the structure 10, for example by means of silicone diaphragms 10a that isolate its thermal conditions, into five regions: the toe 10b, the inner sole 10c, the outer sole 10e, the instep 10f and the heel 10g.

The apparatus further comprises means for heating independently each one of said regions 10b, 10c, 10e, 10f and 10g of the rigid structure 10 to a presettable temperature; said heating means are constituted, in the case being considered, by resistive elements, designated by the reference numerals 13b, 13c, 13e, 13f and 13g respectively, which are electrically powered and can be adjusted for example by means of thermoregulators 14b, 14c, 14e, 14f and 14g.

The resistive elements are conveniently embedded in the material that constitutes the structure 10.

The structure 10 is surrounded by a cladding 12 made of soft material (having for example a hardness of 20–30 ShA) that is permeable to liquids, such as an open-cell polyurethane, or felt, or textile material capable of absorbing water (to approximately 400% by weight) and of distributing it over the entire surface of the structure 10.

Sensor means for sensing the external temperature of each one of the cladding regions that correspond to the regions of the structure 10 are fixed to the cladding 12, for example by means of stitched seams, and are constituted for example by thermocouples, designated by the reference numerals 15b, 15c, 15e, 15f and 15g respectively.

Figure 8:
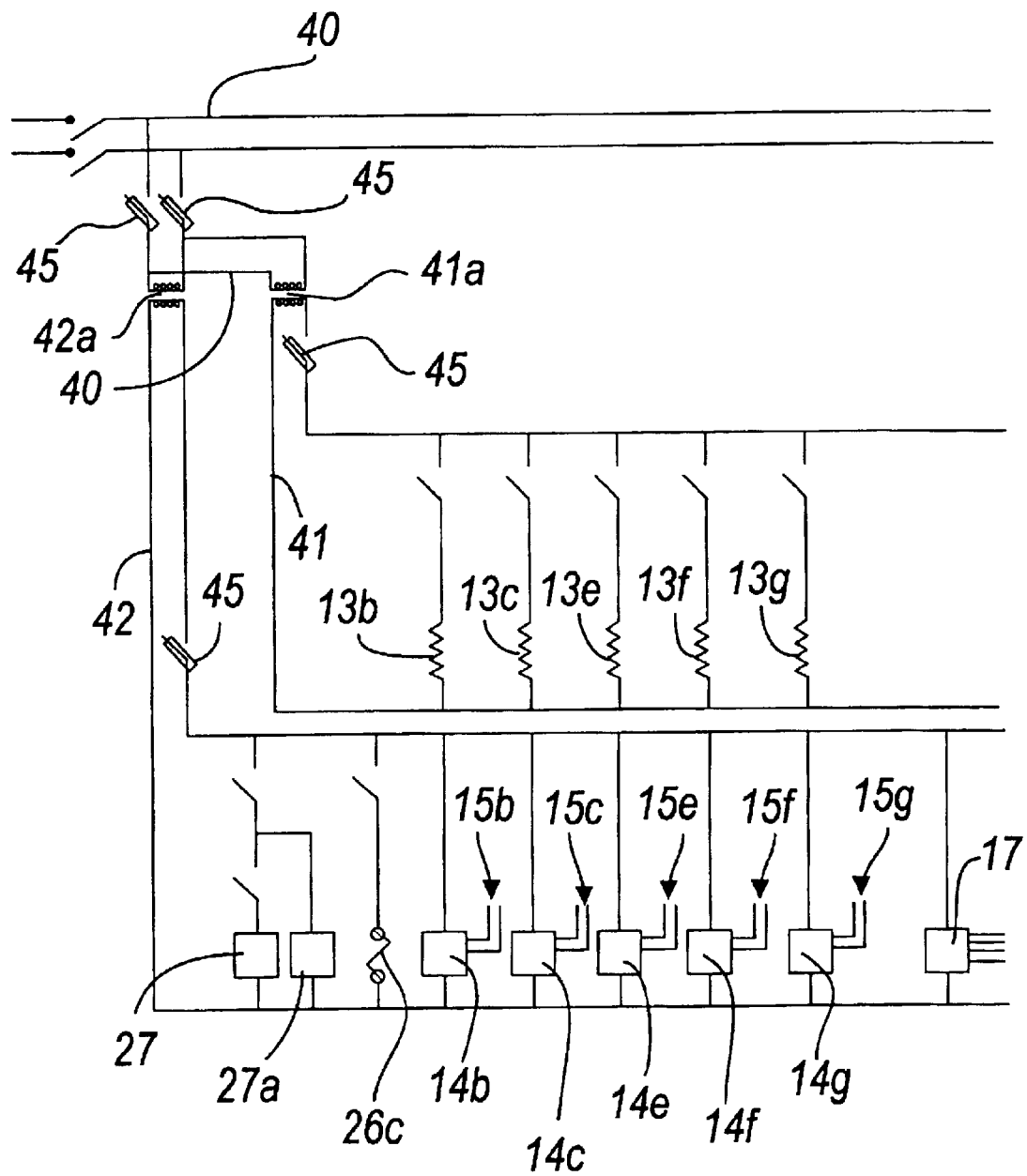
FIG. 8 is an electrical diagram of the apparatus according to the invention.

FIG. 8 is an electrical diagram, which shows that the line of the main power supply at 220 V, designated by the reference numeral 40, is divided into two lines 41 and 42, which are powered respectively at 12 V and 24 V by way of two transformers 41a and 42a.

The thermoregulators 14 are arranged in a parallel configuration on the 24-V line 42; the thermocouples 15, an electric fan 27 with the timer 27a and the corresponding switches, a load cell 17 and a pneumatic electric valve 26c with the corresponding switch are associated with said thermoregulators 14.

The resistive elements 13, together with the corresponding switches, are arranged in parallel on the line 41.

Protective fuses are generally designated by the reference numeral 45.

The elements of this electrical diagram are explained hereafter.

The structure 10 can be fixed, with the interposition of the load cell 17, to a first actuator for vertical reciprocating translational motion, such as a pneumatic cylinder with a stem 18.

Said pneumatic cylinder 18 is rigidly fixed to a beam 19a of a frame 19.

The frame 19 rises from a footing 19b, on which a carriage 23 that supports a free roller 24 can slide in a downward region along straight guides 22.

Said carriage 23 is actuated by a second reciprocating translational motion actuator, such as a stemless pneumatic cylinder 25, so as to perform reciprocating movements, cooperating with the structure 10 to simulate the human walk.

The first and second reciprocating translational motion actuators are functionally connected to speed and synchronization control means 36, which consist of pressure control valves; said valves vary the pressure with which the fluid flows inside them, thus varying its speed and therefore the frequency of the rise and descent of the pneumatic cylinder 18 and the frequency of the forward and return stroke of the stemless pneumatic cylinder 25.

In this manner, since operation of said valves can be synchronized, they allow to simulate walking at a variable speed.

A first stroke limit sensor 26a and a second stroke limit sensor 26b for said carriage 23 are arranged on the footing 19b, respectively at the front and at the rear of the carriage 23.

Said sensors cooperate with a pneumatic electric valve 26c, which regulates the flow of air inside the first and second actuators.

There are also ventilation means for ventilating the structure 10, such as for example an electric fan 27 arranged in front of the region occupied by said structure 10.

There are also supply means for the metered supply of water to the various regions of the structure 10 with its claddings; said means are constituted for example by a precision pump 30 (for example a peristaltic pump that is also capable of pumping simultaneously a plurality of ducts, one or more for each region of the structure 10) driven by an electronic control unit 31.

The water is made to flow into the regions of the structure 10, which are kept at different temperatures, and is distributed by ducts 33, arranged in the structure 10, by way of holes 34 that lead out from it.

There are also measuring means for determining the electric power dissipated in order to maintain a constant temperature of said regions of the structure 10; said means are constituted for example by wattmeters 32, which are connected to the unit 31 like the means for heating the structure 10 and for sensing the temperature.

There are also humidity sensing means for determining relative humidity, which are constituted for example by humidity sensors 35, which are also connected to the unit 31.

Operating principle is as follows: the carriage 23 performs a translational motion, by way of the actuation of the stemless cylinder 25, from the stroke limit position arranged to the rear of the structure 10 toward the front region, thus activating the second sensor 26b; at this point, the stemmed pneumatic cylinder 18 starts to descend, entraining the structure 10 with the shoe 11 to be tested fitted thereon.

When the structure 10 descends, the free roller 24, rigidly coupled to the carriage 23, rolls on the sole of the shoe 11 in order to simulate the walking action.

During this step, the stemmed pneumatic cylinder 18 continues to push, simulating the weight of the user of the shoe; the load cell 17 acts as a feedback control element in order to dose correctly the distribution of the load on the shoe during the walk simulation.

When the carriage 23 reaches the first front stroke limit sensor 26a, the stemmed pneumatic cylinder 18 rises, carrying the structure 10 with it.

Then the carriage 23 is returned by the stemless cylinder 25 toward the rear stroke limit sensor 26b to start a new cycle.

When deemed necessary, it is possible to operate a fan 27 in order to simulate the action of air on the shoe 11; said fan 27 is controlled by a timer 27a.

Figure 9:
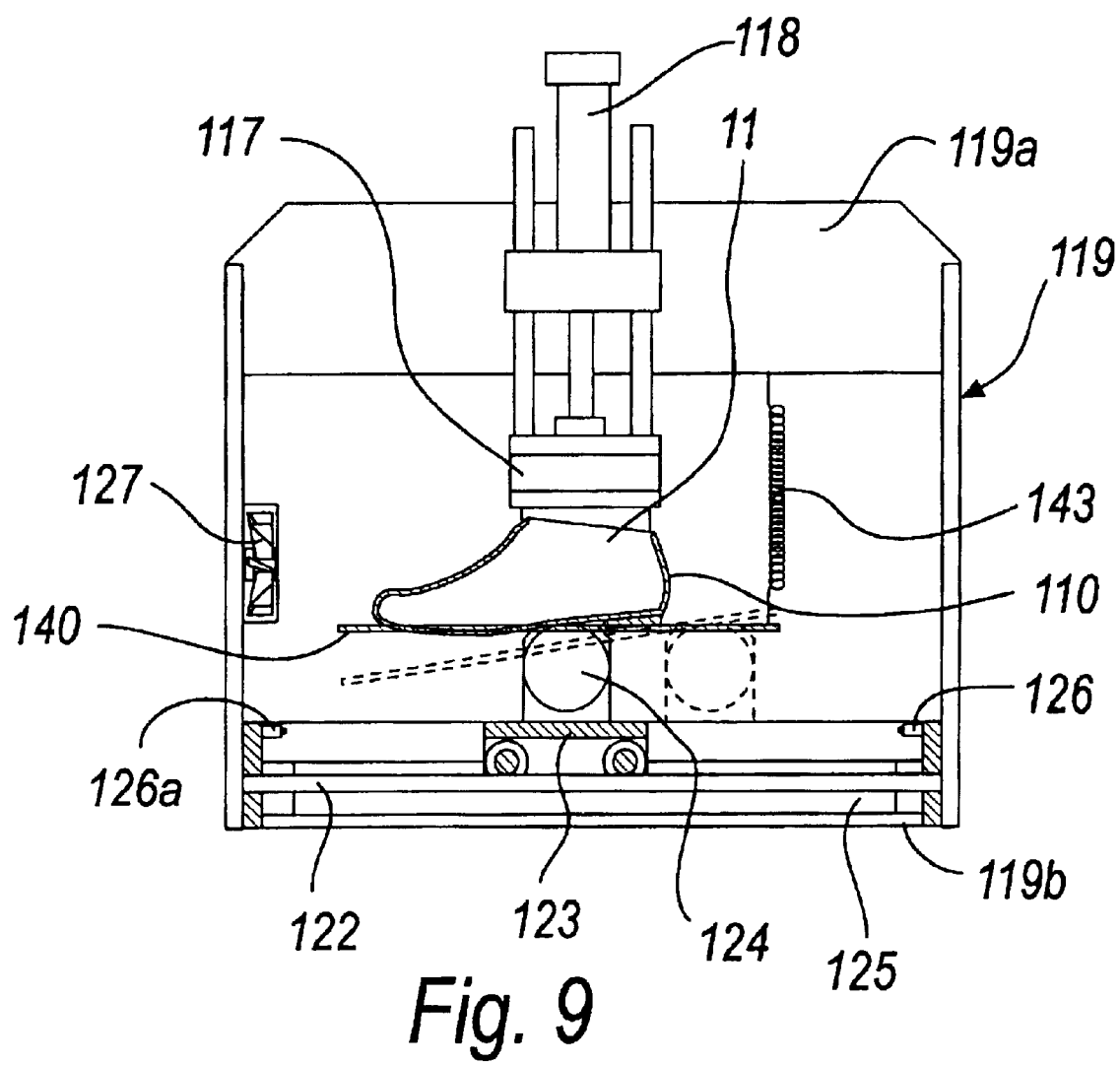
FIG. 9 is a schematic side view of an alternative embodiment of the apparatus according to the invention.
Figure 10:
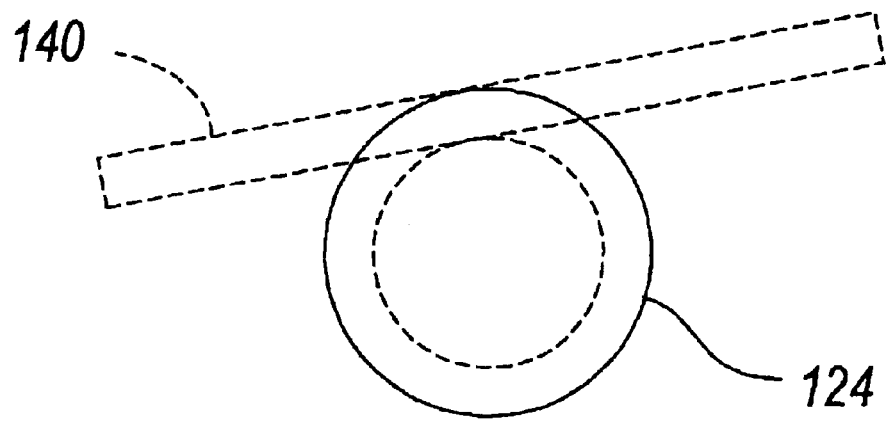
FIG. 10 is an enlarged-scale side view of a detail of FIG. 9.
Figure 11:
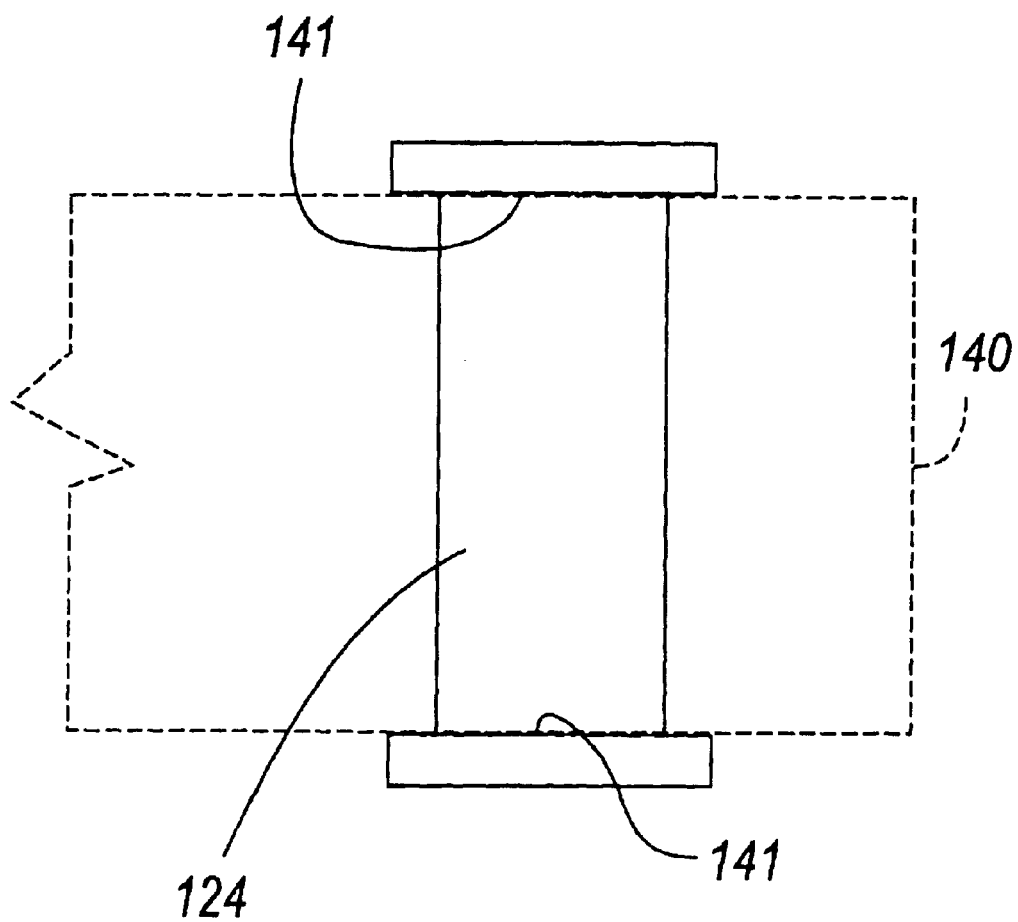
FIG. 11 is a plan view of the detail of FIG. 10.

An alternative embodiment of the invention, shown in FIG. 9, uses a plate 140 that can slide on the surface of the free roller 124 for the resting of the sole of the shoe to be tested 11 during the stroke of the carriage 123.

The plate 140 is rigidly coupled to the frame 119 and to the roller 124 so as to vary the inclination of the contact with the sole of the shoe 11 from an inactive position to a position in which said plate is substantially horizontal.

This inactive position corresponds to a position in which the end of said plate that is directed toward the heel of the shoe 11 is higher than the opposite end.

During the stroke of the carriage 123, the plate 140 varies the inclination of the contact with the sole of the shoe to be tested 11, by way of the combined vertical/horizontal motion of the shoe 11 and of the free roller 124 respectively, which is achieved by way of the stemmed pneumatic cylinder 118 and the stemless cylinder 125.

Said plate 140 can slide in a controlled manner by way of a guide 141 that is formed on the surface of the free roller 124.

Furthermore, the plate 140 is furthermore rigidly coupled to the beam 119a by its first end directed toward the heel of the shoe 11 by way of means for returning to the position that corresponds to the step in which the shoe 11 is fully raised.

Said return means are constituted by elastic elements 143 or, as an alternative, by hydraulic pistons being mounted and acting as the element 143 of FIG. 9.

The variation of the operation of this alternative embodiment is as follows.

During the descent of the structure 110, the sole of the shoe 11 rests against the plate 140, which rotates on the free roller 124 until it arranges itself horizontally.

During this step, the elastic elements 143 tend to draw upward the plate 140 and thus contrast the rotation of said plate.

When the carriage 123 arrives at the first front stroke limit sensor 126a, the stemmed pneumatic cylinder 118 rises, carrying the structure 10 with it.

Then the carriage 123 is returned by the stemless cylinder 125 toward the rear stroke limit sensor 126b in order to start a new cycle.

In this step, the plate 140 again changes inclination with respect to the sole of the shoe 11, and this corresponds to the lifting of the foot from the ground.

In this manner, the action of the ground on the shoe 11 during walking is simulated.

During these operations, the water flows into the heated structure 10 in quantities that can be preset by the operator and wets the cladding 12, which distributes it by way of its structure.

The water evaporates, simulating human perspiration in a manner that is physiologically almost perfect.

The water stream is regulated in two separate manners: for tests at constant humidity and for tests at constant flow-rate.

For constant-humidity tests, the shoe 11 to be tested is fitted onto the structure 10 and the relative humidity sensors are inserted; said sensors, by cooperating with the thermocouples 15, are capable of monitoring the microclimate that is generated between the wall of the shoe 11 and the structure 10 with its claddings.

Said sensors send a signal to the control unit 31, which activates the precision pump 30: when the internal humidity drops below a set minimum value, the pump 30 is activated in order to send water to the structure 10 and return the humidity to the set value.

Clearly, the amount of humidity and heat that the structure 10 dissipates depends on its physiological properties, which are thus monitored and measured precisely by means of the dissipation of electric power and water.

For constant flow-rate tests, the structure 10 with its claddings is supplied with a known quantity of water and its distribution in the various layers is checked during the test together with the resulting humidity values.

All these operations must be performed in a conditioned chamber with constant temperature and humidity.

By using different shoes it is possible to assess the different breathability and absorption capacity.

By using identical shoes modified in some points it is possible to assess their differences and therefore the modifications that have occurred in one shoe with respect to the other.

In practice it has been found that the intended aim and objects of the present invention have been achieved.

The apparatus is in fact capable of simulating the mass and energy exchanges that occur in the human foot and is therefore capable of measuring the breathability and absorption performance of different shoes.

The invention thus conceived is susceptible of numerous modifications and variations, all of which are within the scope of the appended claims.

All the details may further be replaced with other technically equivalent elements.

In practice, the materials used, so long as they are compatible with the contingent use, as well as the dimensions, may be any according to requirements.

The disclosures in Italian Patent Application No. PD2002A000186 from which this application claims priority are incorporated herein by reference.

What is claimed is:

1. An apparatus for measuring breathability and comfort level of a shoe, comprising:
   a rigid structure made of self-supporting heat-conducting material that duplicates a contour of a foot for supporting a shoe to be tested, said rigid structure being divided into at least three rigid structure regions that are thermally insulated from each other,
   heating means for heating autonomously each one of said at least three regions of said rigid structure to a pre-settable temperature,
   at least one cladding surrounding said rigid structure, said cladding including cladding regions corresponding to the rigid structure regions and being made of a soft material whose structure is permeable to liquids and capable of absorbing water and distributing the water over an entire surface of the rigid structure that it surrounds,
   sensor means for sensing an external temperature of said cladding regions that correspond to said at least three rigid structure regions,
   supply means for metering a supply of water to said rigid structure surrounded by said at least one cladding,
   measuring means for determining a level of electric power dissipated from said heating means and keeping constant the sensed external temperature of said cladding regions.

2. The apparatus of claim 1, wherein said rigid structure made of self-supporting material is made of aluminum.

3. The apparatus of claim 1, wherein said sensor means are comprised of thermocouples that are fixed to said at least one cladding.

4. The apparatus of claim 1, wherein said at least one cladding is made of soft material that is capable of absorbing water in an amount equal to approximately 400% by weight and of distributing said water on the surface of the rigid structure.

5. The apparatus of claim 1, wherein said at least one cladding is made of a fabric.

6. The apparatus of claim 1, wherein said rigid structure is divided into five regions comprising toe, inner sole, outer sole, instep and heel regions.

7. The apparatus of claim 1, comprising silicone diaphragms for dividing said at least three regions.

8. The apparatus of claim 1, wherein said heating means are comprised of resistive elements that are powered electrically to provide adjustable temperature.

9. The apparatus of claim 8, comprising thermoregulators for adjusting temperature of said resistive elements.

10. The apparatus of claim 1, further comprising humidity sensing means for sensing relative humidity in each of said at least three regions.

11. The apparatus of claim 10, wherein said supply means for metering a supply of water to said at least three regions of said rigid structure surrounded by said at least one cladding are constituted by a precision pump driven by an electronic control unit.

12. The apparatus of claim 11, wherein said precision pump is peristaltic.

13. The apparatus of claim 11, wherein in testing configuration, the shoe to be tested is fitted on said rigid structure surrounded by said at least one cladding and with said relative humidity sensing means arranged on said rigid structure, the humidity sensing means sending a signal to said control unit, which drives said precision pump, with said pump being activated when humidity internal to said rigid structure drops below a set minimum value in order to send water to said rigid structure and return humidity about said minimum set value.

14. The apparatus of claim 1, comprising: a supporting frame that is composed of a footing and a beam; a first actuator fixed on said beam and configured to vertically move said rigid structure; a second actuator attached to the supporting frame and configured to horizontally move a carriage on said footing, the carriage supporting a free roller for movement with the carriage.

15. The apparatus of claim 14, further comprising a load cell that is interposed between said first actuator and said rigid structure.

16. The apparatus of claim 14, wherein said first actuator is a pneumatic cylinder provided with a stem.

17. The apparatus of claim 14, wherein said second actuator is a stemless pneumatic cylinder.

18. The apparatus of claim 14, further comprising speed control means for controlling speed and synchronization of said first and second actuators.

19. The apparatus of claim 18, wherein said speed control means comprise pressure control valves.

20. The apparatus of claim 14, further comprising a first stroke limit sensor and a second stroke limit sensor for said carriage, which are arranged respectively at a front and at a rear position on said footing.

21. The apparatus of claim 20, further comprising a pneumatic valve that regulates flow of air within said first and second actuators and cooperates with said first and second stroke limit sensors.

22. The apparatus of claim 14, further comprising ventilation means for ventilation of said rigid structure.

23. The apparatus of claim 22, wherein said ventilation means are constituted by an electric fan.

24. The apparatus of claim 14, further comprising a plate configured to be slideable on a surface of said free roller for providing a sole resting region for the shoe to be tested during movement of said carriage that supports said free roller, said plate being rigidly coupled to said roller so as to vary inclination of the sole resting region from an inactive position, in which an end of said plate that is directed toward a heel of the shoe is higher than an opposite end thereof, to a substantially horizontal position of said plate as the roller is moved with the carriage from a starting position, said plate being provided with return means for returning of the plate to said inactive position when the roller is moved with the carriage back to the starting position.

25. The apparatus of claim 24, comprising at least one guide configured to allow controlled sliding of said plate, arranged on the surface of said free roller.

26. The apparatus of claim 24, wherein said plate is rigidly coupled to said beam at the end thereof that is directed toward the heel of the shoe by way of said return means.

27. The apparatus of claim 26, wherein said return means comprise elastic elements.

28. The apparatus of claim 26, wherein said return means comprise hydraulic pistons.

29. An apparatus for measuring breathability and comfort level of a shoe, comprising:
- a rigid structure made of self-supporting heat-conducting material that duplicates a contour of a foot for supporting a shoe to be tested, said rigid structure being divided into at least three rigid structure regions that are thermally insulated from each other,
- heating means for heating autonomously each one of said at least three regions of said rigid structure to a pre-settable temperature,
- at least one cladding surrounding said rigid structure, said cladding including cladding regions corresponding to the rigid structure regions and being made of a soft material whose structure is permeable to liquids and capable of absorbing water and distributing the water over an entire surface of the rigid structure that it surrounds,
- sensor means for sensing an external temperature of said cladding regions that correspond to said rigid structure regions,
- supply means for metering a supply of water to said rigid structure surrounded by said at least one cladding,
- measuring means for determining a level of electric power dissipated from said heating means and keeping constant the sensed external temperature of said cladding regions,
- wherein said heating means are comprised of resistive elements embedded in the self supporting material of the rigid structure, and said resistive elements powered electrically to provide adjustable temperature.

30. The apparatus of claim 29, wherein said rigid structure made of self-supporting material is made of aluminum.

31. The apparatus of claim 29, comprising thermoregulators for adjusting temperature of said resistive elements.

32. The apparatus of claim 29, wherein said sensor means are comprised of thermocouples that are fixed to said at least one cladding.

33. The apparatus of claim 29, wherein said at least one cladding is made of soft material that is capable of absorbing water in an amount equal to approximately 400% by weight and of distributing said water on the surface of the rigid structure.

34. The apparatus of claim 29, wherein said at least one cladding is made of a fabric.

35. The apparatus of claim 29, wherein said rigid structure is divided into five regions comprising toe, inner sole, outer sole, instep and heel regions.

36. The apparatus of claim 29, comprising silicone diaphragms for dividing said at least three regions.

37. The apparatus of claim 29, further comprising humidity sensing means for sensing relative humidity in each of said at least three regions.

38. The apparatus of claim 37, wherein said supply means for metering a supply of water to said at least three regions of said rigid structure surrounded by said at least one cladding are constituted by a precision pump driven by an electronic control unit.

39. The apparatus of claim 38, wherein said precision pump is peristaltic.

40. The apparatus of claim 38, wherein in testing configuration, the shoe to be tested is fitted on said rigid structure with said at least one cladding and surrounded by relative humidity sensing means arranged on said rigid structure, the humidity sensing means sending a signal to said control unit, which drives said precision pump, with said pump being activated when humidity internal to said rigid structure drops below a set minimum value in order to send water to said rigid structure and return humidity about said minimum set value.

41. The apparatus of claim 29, comprising:
- a supporting frame that is composed of a footing and a beam,
- a first actuator fixed on said beam and configured to vertically move said rigid structure,
- a second actuator attached to the supporting frame and configured to horizontally move a carriage on said footing, the carriage supporting a free roller for movement with the carriage.

42. The apparatus of claim 41, further comprising a load cell that is interposed between said first actuator and said rigid structure.

43. The apparatus of claim 41, wherein said first actuator is a pneumatic cylinder provided with a stem.

44. The apparatus of claim 41, wherein said second actuator is a stemless pneumatic cylinder.

45. The apparatus of claim 41, further comprising speed control means for controlling speed and synchronization of said first and second actuators.

46. The apparatus of claim 45, wherein said speed control means comprise pressure control valves.

47. The apparatus of claim 41, further comprising a first stroke limit sensor and a second stroke limit sensor for said carriage, which are arranged respectively at a front and at a rear position on said footing.

48. The apparatus of claim 47, further comprising a pneumatic valve that regulates flow of air within said first and second actuators and cooperates with said first and second stroke limit sensors.

49. The apparatus of claim 41, further comprising ventilation means for ventilation of said rigid structure.

50. The apparatus of claim 49, wherein said ventilation means are constituted by an electric fan.

51. The apparatus of claim 41, further comprising a plate configured to be slideable on a surface of said free roller for providing a sole resting region for the shoe to be tested during movement of said carriage that supports said free roller, said plate being rigidly coupled to said roller so as to vary inclination of the sole resting region from an inactive position, in which an end of said plate that is directed toward a heel of the shoe is higher than an opposite end thereof, to a substantially horizontal position of said plate as the roller is moved with the carriage from a starting position, said plate being provided with return means for returning of the plate to said inactive position when the roller is moved with the carriage back to the starting position.

52. The apparatus of claim 51, comprising at least one guide configured to allow controlled sliding of said plate, arranged on the surface of said free roller.

53. The apparatus of claim 51, wherein said plate is rigidly coupled to said beam at the end thereof that is directed toward the heel of the shoe by way of said return means.

54. The apparatus of claim 53, wherein said return means comprise elastic elements.

55. The apparatus of claim 53, wherein said return means comprise hydraulic pistons.

56. An apparatus for measuring breathability and comfort level of a shoe, comprising:
- a rigid structure made of self-supporting heat-conducting material that duplicates a contour of a foot for supporting a shoe to be tested, said rigid structure being divided into at least three rigid structure regions that are thermally insulated from each other,
- heating means for heating autonomously each one of said at least three regions of said rigid structure to a presettable temperature,
- at least one cladding surrounding said rigid structure, said cladding including cladding regions corresponding to the rigid structure regions and being nude of a soft material whose structure is permeable to liquids and capable of absorbing water and distributing the water over an entire surface of the rigid structure that it surrounds,
- sensor means for sensing an external temperature of regions of said at least one cladding that correspond to said at least three rigid structure regions,
- supply means for metering a supply of water to said rigid structure surrounded by said at least one cladding,
- measuring means for determining a level of electric power dissipated from said heating means and keeping constant the sensed external temperature of said cladding regions,
- a supporting frame that is composed of a footing and a beam:
  - a first actuator fixed on said beam and configured to vertically move said rigid structure,
  - a second actuator attached to the supporting frame and configured to horizontally move a carriage on said footing supporting a free roller for movement with the carriage,
  - and a carriage that supports a free roller, said carriage being horizontally slideable on said footing following the actuation of the carriage by said second actuator.

57. The apparatus of claim 56, wherein said rigid structure made of self-supporting material is made of aluminum.

58. The apparatus of claim 56, wherein said sensor means are comprised of thermocouples that are fixed to said at least one cladding.

59. The apparatus of claim 56, wherein said at least one cladding is made of soft material that is capable of absorbing water in an amount equal to approximately 400% by weight and of distributing said water on the surface of the rigid structure.

60. The apparatus of claim 56, wherein said at least one cladding is made of a fabric.

61. The apparatus of claim 56, wherein said rigid structure is divided into five regions comprising toe, inner sole, outer sole, instep and heel regions.

62. The apparatus of claim 56, comprising silicone diaphragms for dividing said at least three regions.

63. The apparatus of claim 56, further comprising a load cell that is interposed between said first actuator and said rigid structure.

64. The apparatus of claim 56, wherein said first actuator is a pneumatic cylinder provided with a stem.

65. The apparatus of claim 56, wherein said second actuator is a stemless pneumatic cylinder.

66. The apparatus of claim 56, further comprising speed control means for controlling speed and synchronization of said first and second actuators.

67. The apparatus of claim 66, wherein said speed control means comprise pressure control valves.

68. The apparatus of claim 56, further comprising a first stroke limit sensor and a second stroke limit sensor for said carriage, which are arranged respectively at a front and at a rear position on said footing.

69. The apparatus of claim 68, further comprising a pneumatic valve that regulates flow of air within said first and second actuators and cooperates with said first and second stroke limit sensors.

70. The apparatus of claim 56, further comprising ventilation means for ventilation of said rigid structure.

71. The apparatus of claim 70, wherein said ventilation means are constituted by an electric fan.

72. The apparatus of claim 56, wherein said heating means are comprised of resistive elements that are powered electrically to provide adjustable temperature.

73. The apparatus of claim 72, comprising thermoregulators for adjusting temperature of said resistive elements.

74. The apparatus of claim 72, wherein said resistive elements are embedded in the self-supporting material that comprises said rigid structure.

75. The apparatus of claim 56, further comprising humidity sensing means for sensing relative humidity in each of said at least three regions.

76. The apparatus of claim 75, wherein said supply means for metering a supply of water to said at least three regions of said rigid structure surrounded by said at least one cladding are constituted by a precision pump driven by an electronic control unit.

77. The apparatus of claim 76, wherein said precision pump is peristaltic.

78. The apparatus of claim 76, wherein in testing configuration, the shoe to be tested is fitted on said rigid structure with said at least one cladding and surrounded by said relative humidity sensing means arranged on said rigid structure, the humidity sensing means sending a signal to said control unit, which drives said precision pump, with said pump being activated when humidity internal to said rigid structure drops below a set minimum value in order to send water to said rigid structure and return humidity about said minimum set value.

79. The apparatus of claim 56, further comprising a plate configured to be slideable on a surface of said free roller for providing a sole resting region for the shoe to be tested during movement of said carriage that supports said free roller, said plate being rigidly coupled to said roller so as to vary inclination of the sole resting region from an inactive position, in which an end of said plate that is directed toward a heel of the shoe is higher than an opposite end thereof, to a substantially horizontal position of said plate as the roller is moved with the carriage from a starting position, said plate being provided with return means for returning of the plate to said inactive position when the roller is moved with the carriage back to the starting position.

80. The apparatus of claim 79, comprising at least one guide configured to allow controlled sliding of said plate, arranged on the surface of said free roller.

81. The apparatus of claim 79, wherein said plate is rigidly coupled to said beam at the end thereof that is directed toward the heel of the shoe by way of said return means.

82. The apparatus of claim 81, wherein said return means comprise elastic elements.

83. The apparatus of claim 81, wherein said return means comprise hydraulic pistons.

* * * * *